US011505786B2

(12) United States Patent
Song

(10) Patent No.: US 11,505,786 B2
(45) Date of Patent: Nov. 22, 2022

(54) H9 AVIAN INFLUENZA VACCINE STRAIN WHICH DIFFERENTIATES INFECTED FROM VACCINATED ANIMALS, AND PREPARATION METHOD THEREFOR

(71) Applicant: ZHEJIANG DIFFERENCE BIOLOGICAL TECHNOLOGY CO., LTD., Zhejiang (CN)

(72) Inventor: Jiasheng Song, Zhejiang (CN)

(73) Assignee: Zhejiang Difference Biological Technology Co., Ltd.

(*) Notice: Subject to any disclaimer, the term of this patent is extended or adjusted under 35 U.S.C. 154(b) by 0 days.

(21) Appl. No.: 15/733,120

(22) PCT Filed: Jun. 1, 2018

(86) PCT No.: PCT/CN2018/089527

§ 371 (c)(1),
(2) Date: May 20, 2020

(87) PCT Pub. No.: WO2019/100688

PCT Pub. Date: May 31, 2019

(65) Prior Publication Data

US 2020/0318078 A1 Oct. 8, 2020

(30) Foreign Application Priority Data

Nov. 21, 2017 (CN) ........................ 201711166717.3

(51) Int. Cl.

*C12N 7/00* (2006.01)
*A61K 39/145* (2006.01)
*C07K 14/005* (2006.01)
*A61K 39/00* (2006.01)

(52) U.S. Cl.

CPC .............. *C12N 7/00* (2013.01); *A61K 39/145* (2013.01); *C07K 14/005* (2013.01); *A61K 2039/5252* (2013.01); *A61K 2039/5256* (2013.01); *A61K 2039/552* (2013.01); *C12N 2760/16122* (2013.01); *C12N 2760/16134* (2013.01); *C12N 2760/16151* (2013.01); *C12N 2760/16221* (2013.01); *C12N 2760/16234* (2013.01)

(58) Field of Classification Search

None
See application file for complete search history.

(56) References Cited

FOREIGN PATENT DOCUMENTS

| | | |
|---|---|---|
| CN | 102149405 A | 8/2011 |
| CN | 108048476 A | 5/2018 |
| WO | 2016141338 A2 | 9/2016 |

OTHER PUBLICATIONS

Flandorfer et al., Chimeric Influenza A Viruses with a Functional Influenza B Virus Neuraminidase or Hemagglutinin, 2003, Journal of Virology, vol. 77, No. 17, pp. 9116-9123.*

Yan et al., SHORT REPORT Pathogenicity of reassortant H9 influenza viruses with different NA genes in mice and chickens, 2016, vol. 47, No. 67, pp. 1-6.*

Qiao et al., Pathogenicity and transmissibility of reassortant H9 influenza viruses with genes from pandemic H1N1 virus, 2012, vol. 93, pp. 2337-2345.*

Lyndon J. Mitnaul, et al. Balanced Hemagglutinin and Neuraminidase Activities Are Critical for Efficient Replication of Influenza A Virus. Downloaded from <http://jvi.asm.org/ on Feb. 25, 2015 by Univ of New Orleans> . . . Journal of Virology, 0022-538X/00/$04.0010 Jul. 2000, p. 6015-6020.

Ralf Wagner, et al. Functional Balance Between Haemagglutinin and Neuraminidase in Influenza Virus Infections. Rev. Med. Virol. 2002; 12: 159-166. Published online in Wiley InterScience (www.interscience.wiley.com). Accepted: Feb. 15, 2002.

Shin Murakami, et al. Growth Determinants for H5N1 Influenza Vaccine Seed Viruses in MDCK Cells. Journal of Virology, Nov. 2008, p. 10502-10509. vol. 82, No. 21. Department of Microbiology and Immunology, Institute of Medical Science, University of Tokyo, 4-6-1 Shirokanedai, Minato-ku, Tokyo 108-8639, Japan. Published ahead of print on Sep. 3, 2008.

A Rudneva. Influenza A virus reassortants with surface glycoprotein genes of the avian parent viruses: effects of HA and NA gene combinations on virus aggregation. Archives of Virology (1993) 133:437-450. Printed in Austria The D.I. Ivanovsky Institute of Virology and 2 Institute of Biological and Medical Chemistry, Moscow, Russia. Accepted Jun. 8, 1993.

Study on the Preparation of Avian Influenza H9 Subtype Marker Vaccine By Reverse Genetics Manipulation Technique. In Chinese only. Cited in International Search Report and Written Opinion of Chinese PCT Patent Application No. PCT/CN2018/089527 filed Jun. 1, 2018.

E. Nobusawa, et al. Comparison of Complete Amino Acid Sequences and Receptor-Binding Properties among 13 Serotypes of Hemagglutinins of Influenza A Viruses. VIROLOGY 182,475-485 (1991). Department of Virology, Medical School, Nagoya City University, Mizuho-cho. Mizuho-ku, Nagoya-shi, 467 Japan. Received Aug. 17, 1990; accepted Feb. 1, 1991.

Gillian M. Air. Sequence relationships among the hemagglutinin genes of 12 subtypes of influenza A virus. Proc. NatL Acad. Sci. USA vol. 78, No. 12, pp. 7639-7643, Dec. 1981.

* cited by examiner

*Primary Examiner* — Benjamin P Blumel

(74) *Attorney, Agent, or Firm* — Vorys, Sater, Seymour and Pease LLP; Rex W. Miller, II

(57) ABSTRACT

Provided is an application of a label gene sequence in the preparation of an H9 avian influenza vaccine strain which differentiates influenza A virus infection from vaccination, the label gene sequence containing a DNA sequence for coding an influenza B virus NA protein extracellular region amino acid sequence. Also provided are an H9 avian influenza vaccine strain which differentiates influenza A virus infection from vaccination, a preparation method therefor, and an application.

1 Claim, 2 Drawing Sheets

Specification includes a Sequence Listing.

SEQUENCE LISTING

```
<160> NUMBER OF SEQ ID NOS: 8

<210> SEQ ID NO 1
<211> LENGTH: 1743
<212> TYPE: DNA
<213> ORGANISM: artificial sequence
<220> FEATURE:
<223> OTHER INFORMATION: the DNA sequence of HA gene

<400> SEQUENCE: 1

agcaaaagca ggggaatttc acaaccactc aagatggata cagcatcact gataactata     60

ctactagtaa taacagtaag caatgcagat aagatctgca tcggctatca atcaacgaac    120

tccacagaaa ctgtagacac actaacagaa aacaatgtcc ctgtgacaca tgccaaagaa    180

ctgctccaca cagagcataa tgggatgctg tgtgcaacaa gcttgggaca ccctcttatt    240

ctagacacct gtactattga aggactaatc tatggcaatc cctcttgtga tctattcttg    300

ggaggaagag aatggtccta tatcgtcgag agaccatcag ctgtcaacgg attgtgttat    360

cccgggaatg tagaaaatct ggaagagcta aggtcacttt ttagttctgc taggtcttat    420

caaaggatcc agattttccc agacacaatc tggaatgtgt cttacagtgg gacaagcaaa    480

gcatgttcag attcattcta cagaagcatg agatggttga ctcaaaagaa caacgcttac    540

cctattcaag acgcccaata cacaaataat caagaaaaga acattctttt catgtggggc    600

ataaatcacc cacccaccga tactgcgcaa acaaatctgt acacaagaac cgacacaaca    660

acgagtgtgg caacagaaga aataaacagg accttcaaac cattgatagg accaaggcct    720

cttgttaacg gtttgatggg aaggattaat tattattggt ctgtattgaa accgggtcaa    780

acactgcgaa taaaatctaa tggaaatcta atagctccgt ggtatggaca cattctctca    840

ggggagagcc acggaagaat cctgaagact gatttaaaaa ggggtagctg cacagtacaa    900
```

-continued

```
tgtcagacag agaagggtgg cttaaacaca acattgccat tccaaaatgt gagtaagtat    960

gcatttggaa actgctcaaa atacattggc ataaagagtc tcaaacttgc agttggtctg   1020

aggaatgtac cttctagatc tagtagagga ctattcgggg ccatagcagg attcatagaa   1080

ggaggttggt cagggctagt tgctggttgg tatggattcc agcattcaaa tgaccaaggg   1140

gttggtatgg cagcggatag agactcaacc caaaaggcaa ttgataaaat aacatccaaa   1200

gtgaataaca tagtcgacaa aatgaacaag cagtatgaaa ttatcgatca tgagttcagc   1260

gaggttgaaa ctagacttaa catgatcaac aataagattg atgatcaaat ccaagatata   1320

tgggcatata atgcagaatt gctagttctg cttgaaaacc agaaaacact cgatgaacat   1380

gatgcaaatg taaacaatct atataataaa gtgaaaaggg cattgggttc caatgcggtg   1440

gaagatggga aaggatgttt cgagttatac cacaaatgtg atgaccagtg catggagaca   1500

attcgaaacg ggacctacaa cagaaggaag tatcaagagg agtcaaaatt agaaagacag   1560

aaaatagagg gggtcaagct ggaatctgaa ggaacttaca aaatcctcac catttattcg   1620

actgtcgcct catctcttgt aattgcaatg ggtttgctg  ccttcttgtt ctgggccatg   1680

tccaatgggt cttgcagatg caacatttgt atataattgg caaaaacacc ctttgtttct   1740

act                                                                 1743
```

<210> SEQ ID NO 2
<211> LENGTH: 560
<212> TYPE: PRT
<213> ORGANISM: artificial sequence
<220> FEATURE:
<223> OTHER INFORMATION: the amino acid sequence encoded by the H9 subtype HA gene

<400> SEQUENCE: 2

```
Met Asp Thr Ala Ser Leu Ile Thr Ile Leu Leu Val Ile Thr Val Ser
1               5                   10                  15

Asn Ala Asp Lys Ile Cys Ile Gly Tyr Gln Ser Thr Asn Ser Thr Glu
            20                  25                  30

Thr Val Asp Thr Leu Thr Glu Asn Asn Val Pro Val Thr His Ala Lys
        35                  40                  45

Glu Leu Leu His Thr Glu His Asn Gly Met Leu Cys Ala Thr Ser Leu
    50                  55                  60

Gly His Pro Leu Ile Leu Asp Thr Cys Thr Ile Glu Gly Leu Ile Tyr
65                  70                  75                  80

Gly Asn Pro Ser Cys Asp Leu Phe Leu Gly Gly Arg Glu Trp Ser Tyr
                85                  90                  95

Ile Val Glu Arg Pro Ser Ala Val Asn Gly Leu Cys Tyr Pro Gly Asn
            100                 105                 110

Val Glu Asn Leu Glu Glu Leu Arg Ser Leu Phe Ser Ser Ala Arg Ser
        115                 120                 125

Tyr Gln Arg Ile Gln Ile Phe Pro Asp Thr Ile Trp Asn Val Ser Tyr
    130                 135                 140

Ser Gly Thr Ser Lys Ala Cys Ser Asp Ser Phe Tyr Arg Ser Met Arg
145                 150                 155                 160

Trp Leu Thr Gln Lys Asn Asn Ala Tyr Pro Ile Gln Asp Ala Gln Tyr
                165                 170                 175

Thr Asn Asn Gln Glu Lys Asn Ile Leu Phe Met Trp Gly Ile Asn His
            180                 185                 190

Pro Pro Thr Asp Thr Ala Gln Thr Asn Leu Tyr Thr Arg Thr Asp Thr
```

-continued

```
        195                 200                 205

Thr Thr Ser Val Ala Thr Glu Glu Ile Asn Arg Thr Phe Lys Pro Leu
    210                 215                 220

Ile Gly Pro Arg Pro Leu Val Asn Gly Leu Met Gly Arg Ile Asn Tyr
225                 230                 235                 240

Tyr Trp Ser Val Leu Lys Pro Gly Gln Thr Leu Arg Ile Lys Ser Asn
                245                 250                 255

Gly Asn Leu Ile Ala Pro Trp Tyr Gly His Ile Leu Ser Gly Glu Ser
            260                 265                 270

His Gly Arg Ile Leu Lys Thr Asp Leu Lys Arg Gly Ser Cys Thr Val
        275                 280                 285

Gln Cys Gln Thr Glu Lys Gly Gly Leu Asn Thr Thr Leu Pro Phe Gln
    290                 295                 300

Asn Val Ser Lys Tyr Ala Phe Gly Asn Cys Ser Lys Tyr Ile Gly Ile
305                 310                 315                 320

Lys Ser Leu Lys Leu Ala Val Gly Leu Arg Asn Val Pro Ser Arg Ser
                325                 330                 335

Ser Arg Gly Leu Phe Gly Ala Ile Ala Gly Phe Ile Glu Gly Gly Trp
            340                 345                 350

Ser Gly Leu Val Ala Gly Trp Tyr Gly Phe Gln His Ser Asn Asp Gln
        355                 360                 365

Gly Val Gly Met Ala Ala Asp Arg Asp Ser Thr Gln Lys Ala Ile Asp
    370                 375                 380

Lys Ile Thr Ser Lys Val Asn Asn Ile Val Asp Lys Met Asn Lys Gln
385                 390                 395                 400

Tyr Glu Ile Ile Asp His Glu Phe Ser Glu Val Glu Thr Arg Leu Asn
                405                 410                 415

Met Ile Asn Asn Lys Ile Asp Asp Gln Ile Gln Asp Ile Trp Ala Tyr
            420                 425                 430

Asn Ala Glu Leu Leu Val Leu Leu Glu Asn Gln Lys Thr Leu Asp Glu
        435                 440                 445

His Asp Ala Asn Val Asn Asn Leu Tyr Asn Lys Val Lys Arg Ala Leu
    450                 455                 460

Gly Ser Asn Ala Val Glu Asp Gly Lys Gly Cys Phe Glu Leu Tyr His
465                 470                 475                 480

Lys Cys Asp Asp Gln Cys Met Glu Thr Ile Arg Asn Gly Thr Tyr Asn
                485                 490                 495

Arg Arg Lys Tyr Gln Glu Glu Ser Lys Leu Glu Arg Gln Lys Ile Glu
            500                 505                 510

Gly Val Lys Leu Glu Ser Glu Gly Thr Tyr Lys Ile Leu Thr Ile Tyr
        515                 520                 525

Ser Thr Val Ala Ser Ser Leu Val Ile Ala Met Gly Phe Ala Ala Phe
    530                 535                 540

Leu Phe Trp Ala Met Ser Asn Gly Ser Cys Arg Cys Asn Ile Cys Ile
545                 550                 555                 560
```

<210> SEQ ID NO 3
<211> LENGTH: 203
<212> TYPE: DNA
<213> ORGANISM: artificial sequence
<220> FEATURE:
<223> OTHER INFORMATION: 5'-end packaging signal sequence

<400> SEQUENCE: 3

```
agcaaaagca ggggtttaaa atgaatccaa atcagaaaat aataaccatt ggatcaatct     60
```

gtctggtagt cggactaatt agcctaatat tgcaaatagg gaatataatc tcaatatgga 120
ttagccattc aattcaaact ggaagtcaaa accatactgg aatatgcaac caaaacatca 180
ttacctataa aaatagcacc tgg 203

<210> SEQ ID NO 4
<211> LENGTH: 185
<212> TYPE: DNA
<213> ORGANISM: artificial sequence
<220> FEATURE:
<223> OTHER INFORMATION: 3'-end packaging signal sequence

<400> SEQUENCE: 4
gaggccgtgc ttctgggttg aattaatcag gggacgacct aaagaaaaaa caatctggac 60
tagtgcgagc agcatttctt tttgtggcgt gaatagtgat actgtagatt ggtcttggcc 120
agacggtgct gagttgccat tcagcattga caagtagtct gttcaaaaaa ctccttgttt 180
ctact 185

<210> SEQ ID NO 5
<211> LENGTH: 1224
<212> TYPE: DNA
<213> ORGANISM: artificial sequence
<220> FEATURE:
<223> OTHER INFORMATION: the sequence containing type B NA extracellular region

<400> SEQUENCE: 5
gttcaggctg taaatcattc tgcagcaaaa ggggtgacac ttcttctccc agaaccggaa 60
tggacatacc ctcgtttatc ttgcccgggc tcaacctttc agaaagcact cctaattagc 120
ccccatagat tcggagaaat caaaggaaac tcagctccct tgataataag ggaacctttt 180
attgcttgtg gaccaacgga atgcaaacac tttgctctaa cccattatgc agctcaacca 240
gggggatact acaatggaac aagagaagac agaaacaagc tgaggcatct aatttcagtc 300
aaattgggca aaatcccaac agtagaaaac tccattttcc acatggcagc ttggagcggg 360
tccgcatgcc atgatggtaa agaatggaca tatatcggag ttgatggccc cgacagtaat 420
gcattgctca aaataaaata tggagaagca tatactgaca cataccattc ctatgcaaaa 480
aacatcctaa ggacacaaga aagtgcctgc aattgcatcg gggagattg ttatcttatg 540 ataactgatg gcccagcttc aggggttagt gaatgcagat tccttaagat tcgagagggc 600
agaataataa aagaaatatt tccaacagga agagtaaaac atactgagga atgcacatgc 660
ggatttgcca gcaacaaaac catagaatgt gcttgtagag ataaccgtta cacagcaaaa 720
agaccctttg tcaaattaaa tgtggagact gatacagcgg aaataagatt gatgtgcaca 780
gagacttatt tggacacccc cagaccaaat gatggaagca taacagggcc ttgcgaatct 840
gatggggaca aagggagtgg aggcatcaag ggaggatttg ttcatcaaag aatggcatcc 900
aagattggaa ggtggtactc tcgaacgatg tctaaaacca aaagaatggg gatgggactg 960
tatgtaaaat atgatggaga cccatggact gacagtgaag cccttgctct tagtggagta 1020
atggtttcaa tggaagaacc tggttggtat tcctttggct tcgaaataaa agataagaaa 1080
tgtgatgtcc cctgtattgg gatagaaatg gtacatgatg gtgggaaaac gacttggcac 1140
tcagcagcaa cagccattta ttgtttaatg ggctcaggac aattgctgtg ggacactgtc 1200
acaggtgttg atatggctct gtaa 1224

-continued

<210> SEQ ID NO 6
<211> LENGTH: 1224
<212> TYPE: DNA
<213> ORGANISM: artificial sequence
<220> FEATURE:
<223> OTHER INFORMATION: the DNA sequence for coding the extracellular region protein amino acid sequence in influenza B virus NA

<400> SEQUENCE: 6

```
gttcaggctg tgaaccgttc tgcaacaaaa ggggtgacac ttcttctccc agaaccggag     60

tggacatacc cgcgtttatc ttgcccgggc tcaacctttc agaaagcact cctaattagc    120

cctcatagat tcggagaaac caaaggaaac tcagctccct tgataataag ggaacctttt    180

attgcttgtg gaccaaatga atgcaaacac tttgctctaa cccattatgc agcccaacca    240

gggggatact acaatggaac aagaggagac agaaacaagc tgaggcatct aatttcagtc    300

aaattgggca aaatcccaac agtagaaaac tccattttcc acatggcagc atggagcggg    360

tccgcgtgcc atgatggtaa ggaatggaca tatatcggag ttgatggccc tgacaataat    420

gcattgctca aagtaaaata tggagaagca tatactgaca cataccattc ctatgcaaac    480

aaaatcctaa gaacacaaga aagtgcctgc aattgcatcg gggaaattg ttatcttatg     540

ataactgatg gctcagcttc aggtgttagt gaatgcagat ttcttaagat tcgagagggc    600

cgaataataa aagaaatatt tccaacagga agagtaaaac acactgagga atgcacatgc    660

ggatttgcca gcaataaaac catagaatgt gcctgtagag ataacagtta cacagcaaaa    720

agaccttttg tcaaattaaa cgtggagact gatacagcag aaataagatt gatgtgcaca    780

gatacttatt tggacacccc cagaccaaac gatggaagca taacaggccc ttgtgaatct    840

aatggggaca aagggagtgg aggcatcaag ggaggatttg ttcatcaaag aatggaatcc    900

aagattggaa ggtggtactc tcgaacgatg tctaaaactg aaaggatggg gatgggactg    960

tatgtcaagt atgatggaga cccatgggct gacagtgatg ccctagcttt tagtggagta   1020

atggtttcaa tgaaagaacc tggttggtac tcctttggct tcgaaataaa agataagaaa   1080

tgcgatgtcc cctgtattgg gatagagatg gtacatgatg gtggaaaaga gacttggcac   1140

tcagcagcaa cagccattta ctgtttaatg ggctcaggac agctgctgtg ggacactgtc   1200

acaggtgttg acatggctct gtaa                                          1224
```

<210> SEQ ID NO 7
<211> LENGTH: 36
<212> TYPE: DNA
<213> ORGANISM: artificial sequence
<220> FEATURE:
<223> OTHER INFORMATION: Up-primer

<400> SEQUENCE: 7

```
cacacacgtc tccgggagca aaagcagggg aatttc                               36
```

<210> SEQ ID NO 8
<211> LENGTH: 41
<212> TYPE: DNA
<213> ORGANISM: artificial sequence
<220> FEATURE:
<223> OTHER INFORMATION: Low-Primer

<400> SEQUENCE: 8

```
cacacacgtc tcctattagt agaaacaaag ggtgtttttg c                         41
```

H9 AVIAN INFLUENZA VACCINE STRAIN WHICH DIFFERENTIATES INFECTED FROM VACCINATED ANIMALS, AND PREPARATION METHOD THEREFOR

CROSS-REFERENCE TO RELATED APPLICATIONS

This application claims priority to Chinese PCT Patent Application No. PCT/CN2018/089527 filed Jun. 1, 2018, and Chinese Patent Application No. 201711166717.3 filed Nov. 21, 2017, the disclosures of which are incorporated by reference.

SEQUENCE LISTING

The Sequence Listing submitted in text format (.txt) filed on May 20, 2020, named "SequenceListing.txt", created on May 15, 2020 (13 KB), is incorporated herein by reference.

TECHNICAL FIELD

The disclosure belongs to the field of genetic engineering vaccines, specifically relates to an H9 avian influenza vaccine strain which differentiates infection from vaccination, and a preparation method therefor and an application thereof.

BACKGROUND

Avian influenza virus belongs to the genus of influenza virus, the family of Orthomyxoviridae. Influenza viruses are classified into types A, B, and C in terms of antigenic diversity, wherein influenza A viruses have a broad species tropism (including avian, human, swine, etc.), with a strong pathogenicity and huge damages. Influenza B viruses are primarily limited to the human population, although rare infections of seals have been documented, with a relatively low pathogenicity. Influenza C viruses are only found in human and swine. The genomes of influenza A and B can be divided into 8 gene segments in total: PB2, PB1, PA, NP, HA, NA, M, and NS. Once being infected, hosts may generate a large amount of antibodies to HA, NA, M1 and NP proteins, wherein HA may induce major neutralizing antibodies directly. Four major antibodies against HA, NA, M1 and NP induced by viruses of types A and B have no serological cross-reactivity. The antigenic diversity of the HA and NA proteins of the influenza virus is used to classify influenza viruses into different subtypes (HnNn). So far there are 18 subtypes for HA and 11 subtypes for NA. The sequence homologies among different subtypes of HA proteins are between 40%-80% (Air G M. Proceedings of the National Academy of Sciences of the United States of America, 1981, 78(12):7639. Nobusawa E, et al. Virology, 1991, 182(2):475-485). There are no subtypes for influenza B, with high homologies between each virus strain gene. According to the antigenic variant, influenza B viruses are currently divided into only two lineages, Victoria group (named following B/Victoria/2/1987) and Yamagata group (named following B/Yamagata/16/1988) respectively. There are almost all subtypes of influenza A viruses in avian species, playing important roles in the storage and evolution of the virus. H9N2 avian influenza viruses widely exist in various avian, being highly popular in farms. H9 avian influenza causes avian respiratory diseases, resulting in a drop in egg production of adult laying hens and slow growth of broilers, which are often infected in admixture with other viral diseases or bacterial diseases, thus significantly enhancing the fatality rates. Moreover, there are also reports about many cases of direct human infections with H9N2 avian influenza viruses. More importantly, H9N2 subtypes widely exist in nature, which can provide gene segments for other subtypes of avian influenza (e.g., highly pathogenic H7N9, H5N1, etc.), thus greatly promoting the evolution of avian influenza viruses in nature, enhancing the adaptabilities to hosts, and seriously hindering the prevention, control and decontamination of avian influenza. Even some virus strains, after receiving H9N2 gene segments, have enhanced the adaptabilities to human, causing great potential threatens to the public health.

Vaccination is one of the most effective methods for preventing and controlling avian influenza. At present, avian influenza whole virus inactivated vaccines cannot serologically differentiate infected from vaccinated animals, causing a great obstacle in the monitoring and decontamination of avian influenza viruses. Influenza virus HA protein attaches the virus to the cell surface by binding to sialic-acid-containing receptors and promotes viral penetration by mediating fusion of the endosomal and viral membranes, and the NA protein functions as a homotetramer, facilitating the mobility of virions by removing sialic acid residues from viral glycoproteins and infected cells during both entry and release from cells. Therefore, a balance of competent HA and NA (the matching of HA-NA) activities appears critical and may directly affect the replication capacities, growth properties and other biological properties of influenza viruses (Mitnaul L J, Matrosovich M N, Castrucci M R, et al. Balanced Hemagglutinin and Neuraminidase Activities Are Critical for Efficient Replication of Influenza A Virus[J]. Journal of Virology, 2000, 74(13):6015-20). Therefore, selection of viruses with HA-NA functional balance is one of the keys to develop excellent vaccine strains (Murakami S, et al. Growth Determinants for H5N1 Influenza Vaccine Seed Viruses in MDCK Cells[J]. Journal of Virology, 2008, 82(21):10502). For ensuring the functional balance between vaccine strains HA-NA, the two genes are generally derived from the same virus strain. Introduction of heterogenous NAs may disrupt the functional balance between HA-NA, thus reducing the growth and replication capacities of viruses, even resulting in recombinant viruses unable to survive. In general, such risks would increase continually as the homology of the introduced NA gene is reduced (compared with homogenous NAs). It is found in the study that replacements among different subtypes of NA always affect biological properties in terms of replication and growth, of the rescued recombinant viruses. This is also the reason why there are only few advantageous subtype combinations in nature (e.g., common H9N2, H5N1, H7N9, etc.), rather than random combinations of HA-NA (e.g., rare H9N1, H5N9, etc.) (Wagner R et al, Functional balance between haemagglutinin and neuraminidase in influenza virus infectionsPl. Reviews in Medical Virology, 2002, 12(3):159). Rudneva et al used different combinations of N1 gene and subtypes of HA gene to generate recombinant viruses, and found that the growth properties of the recombinant viruses of the rescued H3, H4, H10 and H13 on chick-embryos are poorer than their wild-type viruses (Rudneva I A et al. Influenza A virus reassortants with surface glycoprotein gene of the avian parent viruses: effects of HA and NA gene combinations on virus aggregation. [J]. Archives of Virology, 1993, 133(3-4):437-450). Due to the great differences of NA protein in types B and A influenza viruses (with the similarity <30%), the success probability of obtaining the A/B chimeric virus by introducing type B NA is small. Moreover, there are always defects in the growth properties of the rescued A/B NA chimeric viruses, and it may needed to be adapted by passages in vitro. However, serial passages may bring the risk of antigenic variation, thus resulting in great differences between the antigenicity of the prepared vaccine strains and the original wild-type epidemic strains. So far, there have not been any reports of successful rescue for chimeric viruses containing type B NA.

Although the existing H9 whole virus inactivated vaccines do have advantages such as being reliable in terms of immune effect and low cost, the fact that they cannot serologically differentiate infected from vaccinated animals seriously affects the monitoring on the virus epidemic, thus hindering the decontamination of H9 avian influenza in the farms. Therefore, it is just needed currently to prepare a new H9 avian influenza vaccine strain which can differentiate infection from vaccination.

SUMMARY

To resolve the above issues, the application firstly develops a preparation method of a new H9 avian influenza vaccine which differentiates infection from vaccination by introducing the NA gene of influenza B virus as a label. Moreover, the present invention has successfully constructed an H9 avian influenza vaccine strain which differentiates infected from vaccinated animals, in which NA gene and HA gene exhibit good compatibility, showing good biological properties in terms of replication and growth. The present invention has great application values and prominent public health significance.

The object of the present invention is to provide an H9 avian influenza vaccine strain which differentiates infection from vaccination and an application thereof.

Another object of the present invention is to provide a preparation method of an H9 avian influenza vaccine strain which differentiates infection from vaccination.

The technical solutions employed in the present invention are as below:

An application of a label gene sequence in the preparation of an H9 avian influenza vaccine strain which differentiates influenza A virus infection from vaccination, the label gene sequence containing a DNA sequence for coding an influenza B virus NA protein extracellular region amino acid sequence, or containing a DNA sequence for coding an amino acid sequence having at least 90% homology, or at least 92% homology, or at least 95% homology, or at least 98% homology with the extracellular region amino acid sequence;

alternatively, the label gene sequence containing a DNA sequence for coding the extracellular region amino acid sequence in influenza B virus NA gene, or containing a sequence having at least 90% homology, or at least 92% homology, or at least 95% homology, or at least 98% homology with the DNA sequence;

alternatively, the label gene sequence is a DNA sequence for coding influenza B virus NA protein, or a DNA sequence for coding an amino acid sequence having at least 90% homology, or at least 92% homology, or at least 95% homology, or at least 98% homology with the NA protein amino acid sequence;

alternatively, the label gene sequence is a DNA sequence of influenza B virus NA gene, or a sequence having at least 90% homology, or at least 92% homology, or at least 95% homology, or at least 98% homology with the DNA sequence.

Furthermore, the H9 avian influenza vaccine strain contains an H9 subtype HA gene.

Furthermore, the influenza B virus includes influenza B viruses of Victoria group and Yamagata group.

Furthermore, the influenza B virus specifically includes, but not limited to, virus strains B/Massachusetts/2/2012, B/Brisbane/60/2008, B/Yamagata/16/1988, B/Malaysia/2506/04.

Furthermore, the label gene sequence further contains packaging signal sequences at its both ends, the packaging signal is a packaging signal of H1 subtype NA, or a packaging signal sequence having at least 80% homology, or at least 85% homology, or at least 90% homology, or at least 95% homology with the packaging signal of H1 subtype NA.

Furthermore, the label gene sequence further contains packaging signal sequences at its both ends, wherein the 5'-end packaging signal sequence includes the noncoding region sequence, the intracellular region sequence, and the transmembrane region sequence.

Furthermore, the intracellular region sequence encodes 5-7 amino acids, with the amino acid sequences within the cell.

Furthermore, the transmembrane region sequence encodes 24-32 amino acids, with the amino acid sequences in the transmembrane region.

Furthermore, the 5'-end packaging signal sequence of the label gene sequence is SEQ ID NO:3, or a sequence having at least 80% homology, or at least 85% homology, or at least 90% homology, or at least 95% homology with SEQ ID NO:3.

Furthermore, the label gene sequence further contains packaging signal sequences at its both ends, wherein the 3'-end packaging signal sequence is SEQ ID NO:4, or a sequence having at least 80% homology, or at least 85% homology, or at least 90% homology, or at least 95% homology with SEQ ID NO:4.

A preparation method of an H9 avian influenza vaccine strain which differentiates influenza A virus infection from vaccination, including the following steps: the label gene sequence is rescued with an HA gene of H9 avian influenza viruses over a reverse genetic system to obtain a recombinant vaccine strain, that is an H9 avian influenza vaccine strain which differentiates influenza A virus infection from vaccination;

the label gene sequence containing a DNA sequence for coding an influenza B virus NA protein extracellular region amino acid sequence, or containing a DNA sequence for coding an amino acid sequence having at least 90% homology, or at least 92% homology, or at least 95% homology, or at least 98% homology with the extracellular region amino acid sequence;

alternatively, the label gene sequence containing a DNA sequence for coding an extracellular region amino acid sequence in influenza B virus NA gene, or containing a sequence having at least 90% homology, or at least 92% homology, or at least 95% homology, or at least 98% homology with the DNA sequence;

alternatively, the label gene sequence is a DNA sequence for coding influenza B virus NA protein, or a DNA sequence for coding an amino acid sequence having at least 90% homology, or at least 92% homology, or at least 95% homology, or at least 98% homology with the NA protein amino acid sequence;

alternatively, the label gene sequence is a DNA sequence of influenza B virus NA gene, or a sequence having at least 90% homology, or at least 92% homology, or at least 95% homology, or at least 98% homology with the DNA sequence.

Furthermore, the label gene sequence further contains packaging signal sequences at its both ends.

Furthermore, the 5'-end packaging signal sequence of the label gene sequence is SEQ ID NO:3, or a sequence having at least 80% homology, or at least 85% homology, or at least 90% homology, or at least 95% homology with SEQ ID NO:3.

Furthermore, the 3'-end packaging signal sequence of the label gene sequence is SEQ ID NO:4, or a sequence having at least 80% homology, or at least 85% homology, or at least 90% homology, or at least 95% homology with SEQ ID NO:4.

An H9 avian influenza vaccine strain which differentiates influenza A virus infection from vaccination, which is named as H9 avian influenza vaccine candidate strain Re-H9-DIVA-J2, has been preserved in China Center for Type Culture Collection, with the preservation number of CCTCC NO: V201743.

An application of the above described vaccine strain in the preparation of avian influenza vaccines.

The applicants have preserved the inventive vaccine strain in China Center for Type Culture Collection, the address of which is Wuhan University, China. The Collection Center received the vaccine strain provided by the applicants on Oct. 19, 2017. The preservation number of the culture issued by the Collection Center is CCTCC NO: V201743, the proposed classification name is H9 avian influenza vaccine candidate strain Re-H9-DIVA-J2, the preserved vaccine strain has been identified as viable on Oct. 28, 2017.

The beneficial effects of the invention are:

(1) The application firstly develops a preparation method of a new H9 avian influenza vaccine which differentiates infection from vaccination by introducing NA of influenza B gene as a label.

(2) The present invention has successfully constructed an H9 avian influenza vaccine strain which differentiates infected from vaccinated animals, in which NA gene and HA gene exhibit good compatibility, showing good biological properties in terms of replication and growth, without in vitro passage adaptation, thus avoiding the antigenic variation may be caused by the passage adaptation. Even when passages for the 3rd generation, it still remains low pathogenicity and high titer growth properties in chick-embryos. The present invention has great application values and prominent public health significance.

(3) Conventional H9 avian influenza whole virus inactivated vaccines do have effects, but cannot serologically differentiate antibodies produced from infection from those produced from vaccination, causing a great obstacle in the monitoring and decontamination of avian influenza. The present invention firstly has successfully constructed an H9 avian influenza vaccine strain which differentiates infection from vaccination by using NA of influenza B as a label, having great significances and application values in the prevention, control and decontamination of the H9 avian influenza.

DESCRIPTION OF THE EMBODIMENTS

Figure 1:
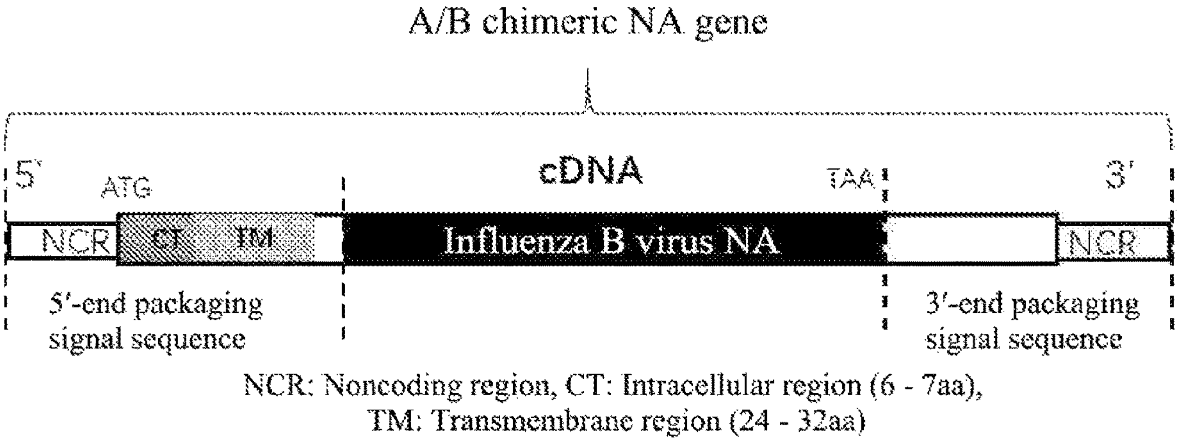
FIG. 1 is the structure schematic diagram of artificially synthesized A/B chimeric NA gene.

An application of a label gene sequence in the preparation of an H9 avian influenza vaccine strain which differentiates influenza A virus infection from vaccination, the label gene sequence containing a DNA sequence for coding an influenza B virus NA protein extracellular region amino acid sequence, or containing a DNA sequence for coding an amino acid sequence having at least 90% homology, or at least 92% homology, or at least 95% homology, or at least 98% homology with the extracellular region amino acid sequence.

An application of a label gene sequence in the preparation of an H9 avian influenza vaccine strain which differentiates influenza A virus infection from vaccination, the label gene sequence containing a DNA sequence for coding the extracellular region amino acid sequence in influenza B virus NA gene, or containing a sequence having at least 90% homology, or at least 92% homology, or at least 95% homology, or at least 98% homology with the DNA sequence.

An application of a label gene sequence in the preparation of an H9 avian influenza vaccine strain which differentiates influenza A virus infection from vaccination, the label gene sequence is a DNA sequence for coding influenza B virus NA protein, or a DNA sequence for coding an amino acid sequence having at least 90% homology, or at least 92% homology, or at least 95% homology, or at least 98% homology with the NA protein amino acid sequence.

An application of a label gene sequence in the preparation of an H9 avian influenza vaccine strain which differentiates influenza A virus infection from vaccination, the label gene sequence is a DNA sequence of influenza B virus NA gene, or a sequence having at least 90% homology, or at least 92% homology, or at least 95% homology, or at least 98% homology with the DNA sequence.

Preferably, the H9 avian influenza vaccine strain contains an H9 subtype HA gene.

Preferably, the amino acid sequence encoded by the H9 subtype HA gene is as shown in SEQ ID NO: 2.

Preferably, the DNA sequence of HA gene is as shown in SEQ ID NO: 1.

Preferably, the influenza B virus includes influenza B viruses of Victoria group and Yamagata group.

Preferably, the influenza B virus specifically includes, but not limited to, virus strains B/Massachusetts/2/2012, B/Brisbane/60/2008, B/Yamagata/16/1988, B/Malaysia/2506/04.

Preferably, the label gene sequence further contains packaging signal sequences at its both ends.

Preferably, the packaging signal is a packaging signal of H1 subtype NA, or a packaging signal sequence having at least 80% homology, or at least 85% homology, or at least 90% homology, or at least 95% homology with the packaging signal of H1 subtype NA.

Preferably, the 5'-end packaging signal sequence of the label gene sequence includes the noncoding region sequence, the intracellular region sequence, and the transmembrane region sequence.

Preferably, the intracellular region sequence encodes 5-7 amino acids, with the amino acid sequences within the cell.

Preferably, the transmembrane region sequence encodes 24-32 amino acids, with the amino acid sequences in the transmembrane region.

More preferably, the 5'-end packaging signal sequence of the label gene sequence is SEQ ID NO: 3, or a sequence having at least 80% homology, or at least 85% homology, or at least 90% homology, or at least 95% homology with SEQ ID NO: 3.

More preferably, the 3'-end packaging signal sequence of the label gene sequence is SEQ ID NO: 4, or a sequence having at least 80% homology, or at least 85% homology, or at least 90% homology, or at least 95% homology with SEQ ID NO: 4.

A preparation method of an H9 avian influenza vaccine strain which differentiates influenza A virus infection from vaccination, including the following steps: the label gene sequence is rescued with an HA gene of H9 avian influenza viruses over a reverse genetic system to obtain a recombinant vaccine strain, that is an H9 avian influenza vaccine strain which differentiates influenza A virus infection from vaccination;

the label gene sequence containing a DNA sequence for coding an influenza B virus NA protein extracellular region amino acid sequence, or containing a DNA sequence for coding an amino acid sequence having at least 90% homology, or at least 92% homology, or at least 95% homology, or at least 98% homology with the extracellular region amino acid sequence;

alternatively, the label gene sequence containing a DNA sequence for coding an extracellular region amino acid sequence in influenza B virus NA gene, or containing a sequence having at least 90% homology, or at least 92% homology, or at least 95% homology, or at least 98% homology with the DNA sequence;

alternatively, the label gene sequence is a DNA sequence for coding influenza B virus NA protein, or a DNA sequence for coding an amino acid sequence having at least 90% homology, or at least 92% homology, or at least 95% homology, or at least 98% homology with the NA protein amino acid sequence;

alternatively, the label gene sequence is a DNA sequence of influenza B virus NA gene, or a sequence having at least 90% homology, or at least 92% homology, or at least 95% homology, or at least 98% homology with the DNA sequence.

Preferably, the label gene sequence further contains packaging signal sequences at its both ends.

Preferably, the packaging signal is a packaging signal of H1 subtype NA, or a packaging signal sequence having at least 80% homology, or at least 85% homology, or at least 90% homology, or at least 95% homology with the packaging signal of H1 subtype NA.

Preferably, the 5'-end packaging signal sequence of the label gene sequence is SEQ ID NO: 3, or a sequence having at least 80% homology, or at least 85% homology, or at least 90% homology, or at least 95% homology with SEQ ID NO: 3.

Preferably, the 3'-end packaging signal sequence of the label gene sequence is SEQ ID NO: 4, or a sequence having at least 80% homology, or at least 85% homology, or at least 90% homology, or at least 95% homology with SEQ ID NO: 4.

Preferably, there are additional 6 PR8 internal genes used during the rescue with the reverse genetic system: PB2, PB1, PA, NP, M and NS.

An H9 avian influenza vaccine strain which differentiates influenza A virus infection from vaccination, which is named as H9 subtype avian influenza vaccine candidate strain Re-H9-DIVA-J2, has been preserved in China Center for Type Culture Collection, with the preservation number of CCTCC NO: V201743.

An application of any one of the above described vaccine strains in the preparation of avian influenza vaccines.

The present invention will be illustrated in detail in conjunction with the following specific examples and the accompanying figures, however, the embodiments of the invention are not limited to this. For unnoted conventional experimental methods, see "Guideline for Molecular Cloning", the 3rd edition (Sambrook, ed., Science press, 2002).

Example 1. A Preparation Method of an H9 Avian Influenza Vaccine Strain Re-H9-DIVA-J2 which Differentiates Influenza A Virus Infection from Vaccination The pFlu vector is a kind of bidirectional transcription vector, which may transcribe viral RNA by the human polI promoter, and also may transcribe viral mRNA by CMV promoter, thus synthesizing the viral proteins (Hoffmann et al., PNAS, USA 97, 6108-6113, 2000).

(1) Cloning HA Gene of H9 Avian Influenza Virus

Figure 2:
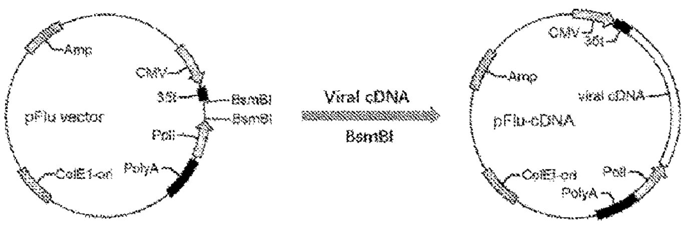
FIG. 2 is the pFLu vector map and the clone schematic diagram of influenza virus gene segments.
Figure 3:
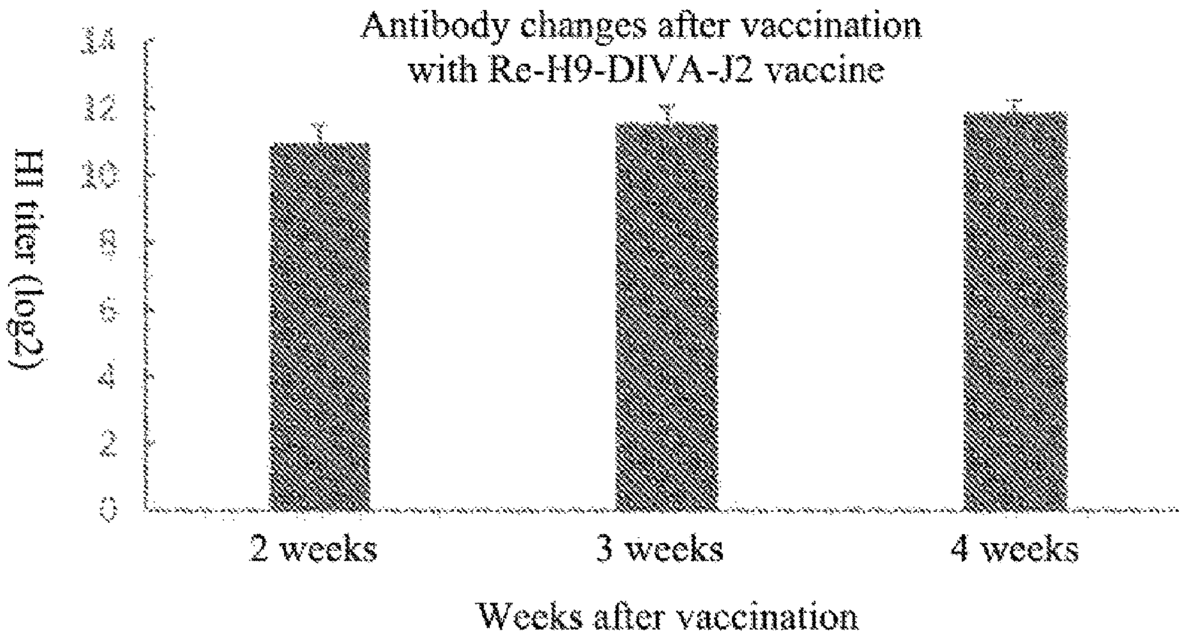
FIG. 3 shows the changes of HI antibody titers after vaccination with Re-H9-DIVA-J2 inactivated vaccine on 3-week-old chicken.

Total RNAs of H9 avian influenza virus A/chicken/Guangdong/J2/2016 (J2 strain for short) are extracted following the instruction of Qiagen RNeasy mini kit. A one step RT-PCR kit (TAKARA) is used to reverse transcribe and amplify the full-length HA gene of J2 strain (SEQ ID NO: 1). RT-PCR primers are Up-primer: CACACACGTCTCCGGGAGCAAAAGCAGGGGAAT-TTC (SEQ ID NO: 7); Low-Primer: CACACACGTCTCC-TATTAGTAGAAACAAAGGGTGTTTTGC (SEQ ID NO: 8), respectively. Reaction conditions were: 50° C. for 30 min, 94° C. for 2 min; 94° C. for 30 sec, 53° C. for 30 sec, 72° C. for 2 min, 30 cycles; 72° C. for 10 min. The amplified HA gene (1.7 kb around) is recycled, then cloned into the pFlu vector by enzyme digestion with BsmBI to obtain a recombinant plasmid pFlu-H9J2-HA (the construction schematic diagram as shown in FIG. 2).

(2) Construction of A/B Chimeric NA Gene

Constructing the artificially synthesized A/B chimeric NA gene as shown in FIG. 1, which contains a DNA sequence (SEQ ID NO: 5) for coding an extracellular region amino acid sequence in influenza B virus NA as the label gene sequence, the sequence containing type B NA extracellular region as shown in SEQ ID NO: 5 deriving from B/Massachusetts/2/2012 in the influenza B virus Yamagata group (Ping J et al, PNAS, 2016, 113(51):E8296-E8305), the label gene sequence further contains packaging signal sequences at its both ends, wherein the 5'-end packaging signal sequence (SEQ ID NO:3) includes the noncoding region sequence, the intracellular region sequence and the transmembrane region sequence, the 3'-end packaging signal sequence is SEQ ID NO:4. The artificially synthesized A/B chimeric NA gene is inserted into the pFlu vector through the BsmBI site to obtain a recombinant plasmid pFlu-PR8-BNA.

(3) Acquisition of Re-H9-DIVA-J2 Vaccine Strain

The recombinant vaccine strain Re-H9-DIVA-J2 is rescued with the classical "6+2" influenza reverse genetic system. Each 0.5 μg of 6 viral PR8 internal genes pFlu-PR8-PB2, pFlu-PR8-PB1, pFlu-PR8-PA, pFlu-PR8-NP, pFlu-PR8-M, pFlu-PR8-ΔNS and 2 external genes pFlu-H9J2-HA, pFlu-PR8-BNA are co-transfected into 293T cells (Lipofectamine 3000), a culture medium containing TPCK-Trypsin at a final concentration of 0.5 μg/ml is exchanged after 24 h, and the cell supernatant is collected after 48 h, obtaining the Re-H9-DIVA-J2 vaccine strain.

The Re-H9-DIVA-J2 vaccine strain prepared in this example will be further detected for its effects below.

Process: The Re-H9-DIVA-J2 vaccine strain (cell supernatant) prepared in this example is inoculated into 9-11-day-old SPF chick-embryos at 0.2 ml per embryo by allantoic cavity inoculation. After inoculation, chick-embryos are cultured in an incubator at 37° C. for 72 hs. The chick-embryo allantoic fluid (F0-generation) is collected for determining its hemagglutinin titer. F0-generation viruses are diluted by a factor of 10,000 and inoculated into 10 SPF chick-embryos, cultured for 72 hs to obtain viruses which are defined as F1-generation. With the same process, F1-generation viruses are serially passaged to F3-generation.

Results: the detection results are shown in Table 1, from which it can be seen that HA titers (log 2) of F0-F3-generations of Re-H9-DIVA-J2 vaccine strains are all greater than 10, with excellent growth properties, indicating that NA gene in the Re-H9-DIVA-J2 vaccine strain obtained in this example exhibited good matching with H9 avian influenza, without the need of passage adaptation in vitro, thus avoiding the disadvantage of antigenic variation caused by the passage adaptation. The inventive Re-H9-DIVA-J2 vaccine strain has low pathogenicity to SPF chick-embryos, there are no deaths of inoculated chick-embryos within 72 hours. After serial passages for the 3rd generation of Re-H9-DIVA-J2 on SPF chick-embryos, it remains low pathogenicity and high titer growth properties in chick-embryos. No SPF chick-embryo deaths caused by viruses are observed during the passages and viral HA titers are all greater than 10 log 2.

In addition, taking F0 and F3-generation viruses of which the artificial chimeric NA genes are amplified by RT-PCR, it is demonstrated by sequencing that chimeric NA gene can be stably passed to progeny viruses. The results indicated that the recombinant Re-H9-DIVA-J2 vaccine strain rescued in the invention has advantages of safety, high titer growth and stable inheritance of marker gene (see Table 1).

TABLE 1

Growth properties of Re-H9-DIVA-J2 vaccine strain (NA extracellular region gene from B/Massachusetts/2/2012) on SPF chick-embryos and the stability of artificial chimeric NA gene (the label gene)

| Virus Passage Number | Titers (HA titers, log2) | Chick-Embryo Deaths Within 72 hs | Stability of Artificial Chimeric NA Gene |
|---|---|---|---|
| F0 | 10 | No deaths | Presence |
| F1 | 11 | No deaths | Not determined |
| F2 | 10.5 | No deaths | Not determined |
| F3 | 11 | No deaths | Presence |

Example 2. A Preparation Method of an H9 Avian Influenza Vaccine Strain Re-H9-DIVA-J2 which Differentiates Influenza A Virus Infection from Vaccination The preparation method of Example 2 is the same as that of Example 1, except that in constructing the artificially synthesized A/B chimeric NA gene as shown in FIG. 1, the DNA sequence for coding the extracellular region protein amino acid sequence in influenza B virus NA is different from that in Example 1, the remaining are all the same as Example 1.

In this Example, the DNA sequence for coding the extracellular region protein amino acid sequence in influenza B virus NA is shown in SEQ ID NO: 6. As the label gene sequence, the sequence shown in SEQ ID NO: 6 derived from B/Brisbane/60/2008 of influenza B virus Victoria group (Ping J et al, PNAS, 2016, 113(51):E8296-E8305).

The Re-H9-DIVA-J2 vaccine strain prepared in this example will be further detected for its effects below.

Process: The Re-H9-DIVA-J2 vaccine strain (cell supernatant) prepared in this example is inoculated into 9-11-day-old SPF chick-embryos at 0.2 ml per embryo by allantoic cavity inoculation. After inoculation, chick-embryos are cultured in an incubator at 37° C. for 72 hs. The chick-embryo allantoic fluid (F0-generation) is collected for determining its hemagglutinin titer. F0-generation viruses are diluted by a factor of 10,000 and inoculated into 10 SPF chick-embryos, cultured for 72 hs to obtain viruses which are defined as F1-generation. With the same process, F1-generation viruses are serially passaged to F3-generation.

Results: the detection results are shown in Table 2. As can be seen from the results that HA titers (log 2) of F0-F3-generations of Re-H9-DIVA-J2 vaccine strains are all greater than 9, indicating that NA gene in the Re-H9-DIVA-J2 vaccine strain obtained in this example exhibited good matching with H9 avian influenza, without the need of passage adaptation in vitro, thus avoiding the disadvantage of antigenic variation caused by the passage adaptation. No SPF chick-embryo deaths caused by viruses are observed during the passages and viral HA titers are all greater than 9 log 2.

Taking F0 and F3-generation viruses of which the chimeric NA genes are amplified by RT-PCR, it is demonstrated by sequencing that chimeric NA gene can be stably passed to progeny viruses. The results indicated that the rescued recombinant viruses have advantages of safety, high titer growth and stable inheritance of marker gene (see Table 2).

TABLE 2

Growth properties of Re-H9-DIVA-J2 vaccine strain (NA extracellular region gene from B/Brisbane/60/2008) on SPF chick-embryos and the stability of artificial chimeric NA gene (the label gene)

| Virus Passage Number | Titers (HA titer, log2) | Chick-Embryo Deaths Within 72 hs | Stability of Artificial Chimeric NA Gene |
|---|---|---|---|
| F0 | 9 | No deaths | Presence |
| F1 | 9 | No deaths | Not determined |
| F2 | 9.5 | No deaths | Not determined |
| F3 | 9 | No deaths | Presence |

As can be seen from the detection data of the above examples 1 and 2, for demonstrating whether type B NA genes of different branches can match with H9 subtype HA (H9-BNA) well, NA genes of representative strains from different groups: B/Brisbane/60/2008 (Victoria group) and Massachusetts/2/2012 (Yamagata group) are selected for study, it is found from the results that NA genes of influenza B viruses of different groups both exhibited good matching with H9, the resulting Re-H9-DIVA-J2 vaccine strains may reach high titers (≥9 log 2) without the need of passage adaptation on chick-embryos.

For representative influenza B virus strains from different groups: B/Brisbane/60/2008 (Victoria group) and Massachusetts/2/2012 (Yamagata group), the homology between the two NA whole gene nucleotide sequences is 94.9%, the homology of the amino acid sequences is 94.9%; the homology between the two DNA sequences for coding NA protein extracellular region is 95.1%, the homology of the NA protein extracellular region amino acid sequences is 94.6%. Because influenza B is only classified into Victoria group and Yamagata group, it is demonstrated in the invention that representative NA strains from the two groups both have good compatibilities with H9 HA, showing that NA type B may all be used in preparing an H9 avian influenza vaccine strain which differentiates influenza A virus infection from vaccination.

Example 3. Preparation of Re-H9-DIVA-J2 Inactivated Vaccine 50 ml of F0-generation allantoic fluids from Re-H9-DIVA-J2 vaccine strains prepared in the above examples are harvested, and inactivated with a formalin solution at a final concentration of 0.25% at 37° C. for 24 hs. The inactivated allantoic fluids are added into 2% of Tween-80, dissolved sufficiently and then emulsified with white oil containing 3% of Span 80 at a proportion of 1:3, at a shear emulsification rate of 12000 rpm for 3 mins. Upon a dosage form test, a sizing test, a viscosity test, and a stability test, it is determined that the inactivated vaccine is an off-white water-in-oil emulsion with low viscosity, uniform particle sizes, good stability and suitable for injection.

Example 4. Detection of Effects of Re-H9-DIVA-J2 Inactivated Vaccine on Vaccinating Animals Process: ten 3-week-old SPF chicken are vaccinated with the above prepared Re-H9-DIVA-J2 inactivated vaccine at 0.2 ml per chick by subcutaneous injection at the neck, blood is sampled on days 14, 21 and 28 respectively, serum is isolated and HI antibodies are determined.

Results: the detection results are shown in Table 3, from which it can be seen that Re-H9-DIVA-J2 inactivated vaccine can promptly stimulate the organism to generate high level of HI antibodies, the average HI titers for weeks 2, 3, 4 are 10.9±0.57, 11.5±0.53, 11.8±0.42 (log 2), respectively. For HA and HI tests, reference to GBT 18936-2003 (diagnosis technology of highly pathogenic avian influenza).

Example 5. Serological Experiments

N1, N2, N6, and N9 genes of the existing influenza A are cloned into pCAGGS eukaryotic expression plasmid through KpnI and NheI sites, which are named as pCAGGS-N1, pCAGGS-N2, pCAGGS-N6, pCAGGS-N9. Each 1 μg of pCAGGS-N1, pCAGGS-N2, pCAGGS-N6, pCAGGS-N9 plasmid is transfected to 293T cells pre-coated on 24-hole cell culture plates. 30 hs after transfection, the reactivities of the following 7 groups of chicken serum with N1, N2, N6, N9 are detected by immunofluorescence.

The profiles of the 7 groups of chicken serum are as below:

Anti-Re-H9-DIVA-J2 chicken serum: chicken serum which is only vaccinated with the inventive Re-H9-DIVA-J2 inactivated vaccine;

Anti-H9N2 chicken serum: chicken serum which is only vaccinated with H9N2 whole virus inactivated vaccine;

H9N2-infected chicken serum: 3-week-old SPF chicken are infected with $10^6EID_{50}$ A/chicken/Guangdong/J2/2016 in nasal cavities, the whole blood is harvested 3 weeks after transfection with H9N2 to prepare the serum.

Anti-N1 chicken serum: one-week-old SPF chicken are vaccinated with 100 μg pCAGGS-N1 (by intramuscular injection) respectively, the whole blood is harvested 4 weeks after vaccination to prepare the serum.

Anti-N2 chicken serum: one-week-old SPF chicken are vaccinated with 100 μg pCAGGS-N2 (by intramuscular injection) respectively, the whole blood is harvested 4 weeks after vaccination to prepare the serum.

Anti-N6 chicken serum: one-week-old SPF chicken are vaccinated with 100 μg pCAGGS-N6 (by intramuscular injection) respectively, the whole blood is harvested 4 weeks after vaccination to prepare the serum.

Anti-N9 chicken serum: one-week-old SPF chicken are vaccinated with 100 μg pCAGGS-N9 (by intramuscular injection) respectively, the whole blood is harvested 4 weeks after vaccination to prepare the serum.

The immunofluorescence process is as below:

1) Into each cell is added 0.5 ml of 4% paraformaldehyde for immobilization for 20 minutes, and then washed with PBS for three times.

2) It is permeated with 0.2% Triton X 100 for 10 minutes, and then washed with PBS for three times.

3) It is blocked with 5% BSA for 1 hour, and then washed with PBS for three times.

4) Primary antibodies are diluted with PBS containing 1% BSA by corresponding factors (anti-Re-H9-DIVA-J2, anti-H9N2, H9N2 infection, dilution for 100-fold; anti-N1/N2/N6/N9, dilution for 20-fold), and added into each hole at 0.5 ml, incubated in a wet box at 37° C. for 1 hour, and then washed with PBS for three times.

5) Anti-Chicken secondary antibodies (Alexa Fluor 594 Donkey Anti-Chicken IgY) are diluted with PBS containing 1% BSA for 200-fold, added into each hole at 0.5 ml, incubated at room temperature for 0.5 hours, and then washed with PBS for three times.

6) Observing with a fluorescence microscope.

Figure 4:
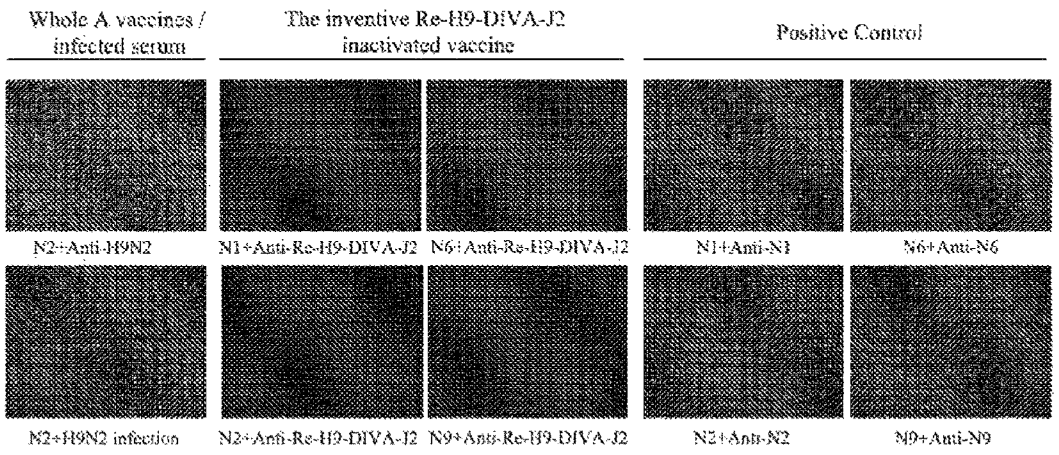
FIG. 4 is detecting the reactivity of anti-Re-H9-DIVA-J2 (artificially synthesized chimeric NA gene) serum with influenza A NA protein by immunofluorescence.

Results: Influenza N1, N2, N6 and N9 neuraminidases are respectively expressed in 293T cells, the immunofluorescence process is used to detect whether serum has reacted with N1, N2, N6 and N9 3 weeks after vaccination with Re-H9-DIVA-J2. It is found that the anti-Re-H9-DIVA-J2 serum does not cross react with N1, N2, N6 and N9 proteins (e.g., as shown in Table 3 and FIG. 4), on the contrary, the serum after vaccinated or infected with H9N2 whole virus may strongly reacted with N2 protein. As in nature, influenza B don't infect avian, it is demonstrated from this experiment that vaccination with the inventive Re-H9-DIVA-J2 vaccine can differentiate infected from vaccinated animals, which overcomes the disadvantage that the existing H9N2 whole virus vaccine is unable to differentiate infected from vaccinated animals.

TABLE 3

The reactivity profiles between each vaccinated chicken serum antibodies and N1, N2, N6 and N9 neuraminidases

| Antibodies | | Antigens | | | |
|---|---|---|---|---|---|
| | | N1 | N2 | N6 | N9 |
| Anti-Re-H9-DIVA-J2 | HI: 11 log2 | No reactivity | No reactivity | No reactivity | No reactivity |
| Anti-H9N2 | HI: 10 log2 | ND | Reactivity | ND | ND |
| H9N2 Infection | HI: 7 log2 | ND | Reactivity | ND | ND |
| Anti-N1 | HI: N/A | Reactivity | ND | ND | ND |
| Anti-N2 | HI: N/A | ND | Reactivity | ND | ND |
| Anti-N6 | HI: N/A | ND | ND | Reactivity | ND |
| Anti-N9 | HI: N/A | ND | ND | ND | Reactivity |

Note:
N/A: not applicable;
ND: not detected.

Example 6. A Preparation Method of an H9 Avian Influenza Vaccine Strain Re-H9-DIVA-J2 which Differentiates Influenza A Virus Infection from Vaccination The preparation method of Example 6 is the same as that of Example 1, except that in constructing the artificially synthesized A/B chimeric NA gene as shown in FIG. 1, the influenza B virus NA sequence used is the DNA sequence for coding NA whole protein sequence, the remaining are all the same as Example 1, wherein, the DNA sequence of NA derived from the NA whole gene sequence of B/Massachusetts/2/2012 in the Yamagata group of influenza B virus (Ping J et al, PNAS, 2016, 113(51): E8296-E8305).

The above examples are the preferable embodiments of the invention, however, the detailed description of the invention is not limited to the examples described above, any other changes, modifications, substitutions, combinations, simplifications made without deviating from the spirit and principle of the invention should all be considered as equivalent replacements, which are all within the scope of the present invention.

What is claimed is:

1. A preparation method of an H9 avian influenza vaccine strain which differentiates influenza A virus infection from vaccination, comprising the following steps: the label gene sequence is rescued with an HA gene of H9 avian influenza viruses over a reverse genetic system to obtain a recombinant vaccine strain, that is an H9 avian influenza vaccine strain which differentiates influenza A virus infection from vaccination;

the label gene sequence containing a DNA sequence for coding an influenza B virus NA protein extracellular region amino acid sequence, or containing a DNA sequence for coding an amino acid sequence having at least 90% identity, or at least 92% identity, or at least 95% identity, or at least 98% identity with the extracellular region amino acid sequence;

alternatively, the label gene sequence containing a DNA sequence for coding an extracellular region amino acid sequence in influenza B virus NA gene, or containing a sequence having at least 90% identity, or at least 92% identity, or at least 95% identity, or at least 98% identity with the DNA sequence;

alternatively, the label gene sequence is a DNA sequence for coding influenza B virus NA protein, or a DNA sequence for coding an amino acid sequence having at least 90% identity, or at least 92% identity, or at least 95% identity, or at least 98% identity with the NA protein amino acid sequence;

alternatively, the label gene sequence is a DNA sequence of influenza B virus NA gene, or a sequence having at least 90% identity, or at least 92% identity, or at least 95% identity, or at least 98% identity with the DNA sequence;

wherein the label gene sequence further contains packaging signal sequences at its both ends;

the 5'-end packaging signal sequence of the label gene sequence is SEQ ID NO: 3, or a sequence having at least 80% identity, or at least 85% identity, or at least 90% identity, or at least 95% identity with SEQ ID NO: 3;

the 3'-end packaging signal sequence of the label gene sequence is SEQ ID NO: 4, or a sequence having at least 80% identity, or at least 85% identity, or at least 90% identity, or at least 95% identity with SEQ ID NO: 4.

* * * * *